United States Patent [19]
Ryder et al.

[11] Patent Number: 5,786,183
[45] Date of Patent: Jul. 28, 1998

[54] METHODS OF ENHANCING NUCLEIC ACID AMPLIFICATION

[75] Inventors: Thomas B. Ryder, Escondido; Elizabeth R. Billyard; Nanibhushan Dattagupta, both of San Diego, all of Calif.

[73] Assignee: Gen-Probe Incorporated, San Diego, Calif.

[21] Appl. No.: 421,471

[22] Filed: Apr. 14, 1995

Related U.S. Application Data

[63] Continuation of Ser. No. 97,262, Jul. 23, 1993, abandoned.
[51] Int. Cl.$^6$ .............................. C12P 19/34; C12Q 1/68
[52] U.S. Cl. ......................... 435/91.2; 435/91.21; 435/6
[58] Field of Search ....................... 435/6, 91.2; 935/77, 935/78

[56] References Cited

U.S. PATENT DOCUMENTS

| | | | |
|---|---|---|---|
| 4,683,202 | 7/1987 | Mullis et al. | 435/91.2 |
| 5,066,584 | 11/1991 | Gyllensten et al. | 435/91.2 |
| 5,474,916 | 12/1995 | Reischl et al. | 435/91.2 |

FOREIGN PATENT DOCUMENTS

| | | |
|---|---|---|
| 0329822 | 8/1989 | European Pat. Off. . |
| 0469610 | 2/1992 | European Pat. Off. . |
| 0519338 | 12/1992 | European Pat. Off. . |
| 0543612 | 5/1993 | European Pat. Off. . |
| 0545010 | 6/1993 | European Pat. Off. . |
| 0628640 | 12/1994 | European Pat. Off. . |
| 8810315 | 12/1988 | WIPO . |
| 8901050 | 2/1989 | WIPO . |
| 8902476 | 3/1989 | WIPO . |
| 9101384 | 2/1991 | WIPO . |

OTHER PUBLICATIONS

Walker et al, Nucleic Acid Res 20: 1691–1786 (1992) "Strand displacement amplification . . . ".
Guatelli et al., PNAS 87:1874–1878 (1990) "Isothermal in vitro amplification . . . ".
Kievits et al, J. Virol. Meth 35:273–286 (1991).
Erlich et al., "Recent Advances in the Polymerase Chain Reaction," *Science* 252;1643–1651 (1991).
Ishino, "Rapid and Reliable DNA Sequencing With a Dideoxy Sequencing Kit," *American Biotechnology Laboratory* 10:47 (1992).
Livache et al., "Detection of HIV$_1$ DNA in Biological Samples by an Homogeneous Assay: Fluorescence Measurement of Double–Stranded RNA Synthesized from Amplified DNA," *Analytical Biochemistry*, 217:248–254 (1994).
Sellmann et al., "Purification and Characterization of DNA Polymerases from Bacillus Species," *Journal of Bacteriology*, 174:4350–4355 (1992).
Wu et al., "Laboratory Methods—The Effect of Temperature and Oligonucleotide Primer Length on the Specificity and Efficiency of Amplification by the Polymerase Chain Reaction," *DNA and Cell Biology* 10:233–2388 (1991).
Arnold et al., "Assay Formats Involving Acridinium–Ester–Labeled DNA Probes," *Clinical Chemistry* 35:1588–1594 (1989).
Conway et al., "Detection of HIV–1 DNA in Crude Cell Lysates of Peripheral Blood Mononuclear Cells by the Polyerase Chain Reaction and Nonradioactive Oligonucleoitide Probes," *Journal of Acquired Immunie Deficiency Syndromes* 3:1059–1064 (1990).
Matsumoto et al., "Deetection of Human T–Cell Leukemia Virus Type I (HTLV–I) Provirus in an Infected Cell Line and in Peripheral Mononuclear Cells of Blood Donors by the Nested Double Polymerase Chain Reaction Method: Comparison with HTLV–I Antibody Tests," *Journal of Virology* 64:5290–5294 (1990).
Garson et al., "Demonstration of viraemia patterns in haemophiliacs treated with hepatitis–C–virus–contaminated factor VIII concentrates," *The Lancet* 336:1022–1025 (1990).
Kievits et al., "NASBA™ isothermal enzymatic in vitro nucleic acid amplification optimized for the diagnosis of HIV–1 infection," *Journal of Virological Methods* 35:275–286 (1991).
Saiki et al., "Primer–Directed Enzymatic Amplification of DNA with a Thermostable DNA Polymerase," *Science* 239:487–491 (1988).
Rychlik et al., "Optimization of the annealing temperature for DNA amplification in vitro," *Nucleic Acids Research* 18:6409–6412 (1990).
Maniatis et al., "Molecular Cloning —A Laboratory Manual" (New York: Cold Spring Harbor Laboratory, 1982).
Lynch et al., "Detection of HIV–1 DNA by PCR: Evaluation of Primer Pair Concordance and Sensitivity of a Single Primer Pair," *Journal of Acquired Immune Deficiency Syndromes* 5:433–440 (1992).
Barany, "The Ligase Chain Reaction in a PCR World," *PCR Methods and Applications* 1:5–16 (1991).
Kaboev et al., "Purification and Properties of Deoxyribonucleic Acid Polymerase from *Bacillus stearothermophilus*," *Journal of Bacteriology* 145:21–26 (1981).
Fahy et al, "Self–sustained Sequence Replication (3SR): An Isothermal Transcription–based Amplification System Alternative to PCR," *PCR Methods and Applications* 1:25–33, 1991.

*Primary Examiner*—Eggerton A. Campbell
*Attorney, Agent, or Firm*—Lyon & Lyon LLP

[57] ABSTRACT

A method for amplification of a nucleic acid strand in a test sample. The method includes contacting the nucleic acid strand from the test sample simultaneously with at least three oligonucleotide primers. At least one primer is a promoter-primer, and at least one other primer is complementary to the nucleic acid strand, and one other primer is complementary to a strand complementary to the nucleic acid strand. The method further includes contacting the nucleic acid strand and primers with one or more proteins having RNA-directed and/or DNA-directed DNA polymerase activities, an RNA polymerase activity, and an RNAse H activity under primer-extension conditions to allow amplification of a target region in the nucleic acid strand at essentially constant temperature.

59 Claims, 4 Drawing Sheets

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
( A ) LENGTH: 24
( B ) TYPE: nucleic
( C ) STRANDEDNESS: single
( D ) TOPOLOGY: linear ( i i ) SEQUENCE DESCRIPTION: SEQ ID NO: 1:

ATTCCCTACA ATCCCCAAAG TCAA    24

( 2 ) INFORMATION FOR SEQ ID NO: 2:

( i ) SEQUENCE CHARACTERISTICS:

(A) LENGTH: 49
(B) TYPE: nucleic
(C) STRANDEDNESS: single
(D) TOPOLOGY: linear (ii) SEQUENCE DESCRIPTION: SEQ ID NO: 2:

AATTTAATAC GACTCACTAT AGGGAGACAA ATGGCAGTAT TCATCCACA  49

(2) INFORMATION FOR SEQ ID NO: 3:

(i) SEQUENCE CHARACTERISTICS:
(A) LENGTH: 23
(B) TYPE: nucleic
(C) STRANDEDNESS: single
(D) TOPOLOGY: linear (ii) SEQUENCE DESCRIPTION: SEQ ID NO: 3:

GTTTGTATGT CTGTTGCTAT TAT  23

(2) INFORMATION FOR SEQ ID NO: 4:

(i) SEQUENCE CHARACTERISTICS:
(A) LENGTH: 45
(B) TYPE: nucleic
(C) STRANDEDNESS: single
(D) TOPOLOGY: linear (ii) SEQUENCE DESCRIPTION: SEQ ID NO: 4:

AATTTAATAC GACTCACTAT AGGGAGACCC TTCACCTTTC CAGAG  45

(2) INFORMATION FOR SEQ ID NO: 5:

(i) SEQUENCE CHARACTERISTICS:
(A) LENGTH: 25
(B) TYPE: nucleic
(C) STRANDEDNESS: single
(D) TOPOLOGY: linear (ii) SEQUENCE DESCRIPTION: SEQ ID NO: 5:

TGCACCAGGC CAGATGAGAG AACCA  25

(2) INFORMATION FOR SEQ ID NO: 6:

(i) SEQUENCE CHARACTERISTICS:
(A) LENGTH: 46
(B) TYPE: nucleic acid
(C) STRANDEDNESS: single
(D) TOPOLOGY: linear (ii) SEQUENCE DESCRIPTION: SEQ ID NO: 6:

AATTTAATAC GACTCACTAT AGGGAGAAGT GACATAGCAG GAACTA  46

(2) INFORMATION FOR SEQ ID NO: 7:

(i) SEQUENCE CHARACTERISTICS:
(A) LENGTH: 23
(B) TYPE: nucleic acid
(C) STRANDEDNESS: single
(D) TOPOLOGY: linear (ii) SEQUENCE DESCRIPTION: SEQ ID NO: 7:

AGATTTCTCC TACTGGGATA GGT  23

(2) INFORMATION FOR SEQ ID NO: 8:

(i) SEQUENCE CHARACTERISTICS:
(A) LENGTH: 49
(B) TYPE: nucleic acid ( C ) STRANDEDNESS: single
( D ) TOPOLOGY: linear ( i i ) SEQUENCE DESCRIPTION: SEQ ID NO: 8:

AATTTAATAC GACTCACTAT AGGGAGATTG GACCAGCAAG GTTTCTGTC   49

METHODS OF ENHANCING NUCLEIC ACID AMPLIFICATION

This application is a continuation of application Ser. No. 08/097,262, filed Jul. 23, 1993 abandoned.

This invention relates to amplification of nucleic acid strands using a DNA polymerase and an RNA polymerase at essentially constant temperature.

BACKGROUND OF THE INVENTION

The ability to detect specific nucleic acid sequences has afforded many practical benefits in areas such as genetic research, clinical diagnostic testing, forensic sciences, archaeology, etc. In many cases, the sequence of interest might be present at a level much too low to detect directly, even using probes with very high specific activity labels. In recent years, strategies have been devised for efficiently generating new copies of target sequences, including very powerful exponential amplification methods, which make it easier to accurately detect the presence of very low target levels.

One such method is the polymerase chain reaction (Mullis et al., U.S. Pat. No. 4,683,202) in which a reaction mix of primers, substrates, DNA polymerase and analyte nucleic acid is subjected to n cycles of heating to a temperature sufficient for denaturing double-stranded nucleic acids and cooling to a temperature at which primer annealing and extension can occur. This reaction is well understood to have a maximum amplification factor of $2^n$ since each strand of a target sequence can be copied into (at most) one new complementary strand during each cycle.

The performance of target-specific amplification has been augmented by performing two or more successive amplification reactions in which the target region defined by the primers used in the subsequent rounds is contained within the target amplicon generated by primers used in the previous round. Even if the amplification of a desired target is inefficient in the first round because of co-amplification of non-target sequences, the target amplicons that are generated should have a selective advantage for further amplification by the next primer set since non-target amplicons are usually not more effective templates for further amplification by the nested primer set than other non-target sequences present. This strategy has been used to improve the ability of amplification methods such as PCR (Conway et al., *J. Acquired Immune Def. Syndromes* 3:1059 (1990); Matsumoto et al., *J. Virol.* 64:5290 (1990); Garson et al., *Lancet* 336:1022 (1990); and NASBA (Kievits et al., *J. Virol. Methods* 35:273 (1991)) to detect very low target levels.

The amplification method of Kacian et al. PCT-/US90/03907 depends on multiple enzyme activities (i.e., including RNA polymerase, DNA-directed DNA polymerase, RNA-directed DNA polymerase, and RNase H). Although it is possible to provide these activities by contacting the other reactants with separate enzymes possessing one each of these activities, a preferred configuration uses a single enzyme, reverse transcriptase, as the principal source of the last three activities listed above. For example, one embodiment of this method employs RNA polymerase from coliphage T7 and reverse transcriptase from Moloney murine leukemia virus (MuLV) in a reaction which supports amplification extents of up to $10^{12}$ fold or more.

The rate of accumulation of products is much more complicated for such an asynchronous, continuous amplification process but is calculable based on straight-forward physical properties of the reaction components.

The exponential accumulation of amplification products does not proceed indefinitely in any of these methods. The rate per time of new copy production reaches a maximum as the enzymes present become saturated by the number of existing templates available to be copied. Thus, the system changes with time to a linear, rather than exponential, rate of accumulation. Ultimately the amount of product made is limited by the number of molecules of those substrates, such as primers and nucleosides, which are physically incorporated into amplification products.

SUMMARY OF THE INVENTION

This invention relates to a significant improvement of the process described by Kacian et al. In particular, it relates to methods for improving the sensitivity of the process, i.e., the ability to amplify desired target sequences that are present in extremely small numbers.

Applicant believes that the most significant and prevalent obstacle to achieving maximum sensitivity is competition for reaction components by amplification of non-target sequences. Although primer annealing and extension should be most efficient on target sequences which are highly complementary to the primer, the possibility that a primer can complex with, and be extended upon, a sequence with only a few bases of complementarity to the 3' end of a primer is thermodynamically predictable and empirically known in the art. Even if the frequency per site of non-target initiation is low, the number of non-target bases in a reaction is usually much greater than the number of targeted bases complementary to the primers used to select the target sequence. Since a primer is physically incorporated into the initiation product, subsequent complementary copies can be very active templates for further amplification even though the original progenitor sequence scarcely resembled the desired target.

The relative specificity of initiation by different primer sequences can vary over quite a great range and while the specificity cannot reliably be predicted based on sequence alone, it is possible to identify preferable sequences by routine experimentation. However, the considerations described above imply that for even the best primers, the potential for interference by non-target initiation becomes increasingly severe as the number of target molecules is reduced since it becomes more probable that at some point early in the reaction, the population of non-target amplicons will be larger than the population of target-specific amplicons. The difference between these population sizes can be amplified exponentially as the reaction proceeds, and it is possible in such a case that the depletion of reaction components by non-target amplification causes the reaction to slow or stop before the target-specific product reaches detectable levels.

It is well known in the art that the stability of a base-paired complex between two nucleic acid sequences decreases as the temperature is increased. This usually results in an apparent increase in the specificity of detectable hybridization since hybrid thermal stability depends on the extent and continuity of base-pairing. Improvements in the yield of target-specific amplicon and reduction in the accumulation of non-target products were observed when the availability of a thermostable DNA polymerase made it possible to use higher reaction temperatures for PCR (Saiki et al., *Science* 239:487 (1988)). Flexibility in selecting a reaction temperature has simplified effective optimization of PCR systems by routine experimentation (Rychlik et al., *Nucleic Acids Res.* 18:6409 (1990)). However, development of systems for reliable detection of very low target levels (e.g., <50) remains challenging.

Although raising the temperature reduces the lifetime of base-paired complexes once formed, higher temperatures also increase the rate of collisions between molecules to form potentially extensible complexes. Applicant has found that the amount of non-target priming increased at temperatures both above and below a measured optimum. Thus, it is rare that one can expect to achieve absolute specificity for the desired target based on controlling the temperature alone.

Other strategies have been described for enhancing the specificity of primer extension including use of chemical denaturants and single-stranded binding proteins. Although these strategies have been useful in some cases, consistently favorable conditions have not been described.

At this time, thermostable variants of reverse transcriptase which retain all three activities noted above are not known. Thermostable RNA polymerases have been described but none as yet having a promoter specificity as well-characterized as T7 RNA polymerase. Methods are known in the art to screen for, select for, and/or engineer enzyme variants with desirable properties, including thermostability, but the methods disclosed herein afford another solution to the challenge of enhancing initiation specificity and, consequently, the sensitivity of target amplification. These methods have been especially effective in compositions having a small number of target sequences in the presence of a vast excess of non-target nucleic acids, and furthermore, can be employed together with elevated temperature treatments.

The methods disclosed herein employ the concept of amplicon nesting, but are significantly different from previously described strategies in which a portion of a reaction run with the first primer set is transferred to a new reaction containing the second primer set. In the methods described herein, all the primers delimiting the nested amplicons can be combined in a single reaction such that serial transfer of products to a new reaction is unnecessary, and furthermore, the best mode is apparently favored by a dynamic coordination among their activities.

Increasing the number and types of primers present in the mixture does significantly increase the potential for various side reactions, including those leading to competitive, non-target amplification. The extra primers added also have the potential to interfere with the desired normal function of the principal primer set. Therefore, it was unexpected that we could identify conditions wherein the degree of enhancement was not only unequivocal but of such a dramatic extent. Note that the method functions through a continuous process and does not require or employ any heat treatments to thermally denature double-stranded primer extension products.

Thus, in a first aspect, the invention features a method for amplification of a target sequence in a nucleic acid strand in a test sample. The method includes contacting the nucleic acid strand from the test sample simultaneously with at least three oligonucleotide primers. At least one primer is a promoter-primer (i.e., having a primer region complementary to the nucleic acid strand or its complement, and another region, 5' of the primer region, recognized in its double-stranded form by an RNA polymerase), and at least one other primer is complementary to the nucleic acid strand, and one other primer is complementary to a strand complementary to the nucleic acid strand. The method further includes contacting the nucleic acid strand and primers with one or more proteins having RNA-directed and/or DNA-directed DNA polymerase activities, an RNA polymerase activity, and an RNAse H activity under primer-extension conditions to allow amplification of a target region in the nucleic acid strand at essentially constant temperature.

A "test sample" includes any clinical, agricultural, or environmental sample which may or may not be pretreated to make the nucleic acid strand available for hybridization with the primers. Such a strand is not amplified by other methods prior to the first contacting step described herein. That is, the method of this invention can be used directly to amplify a nucleic acid within such a sample. No prior amplification by PCR or the method of Kacian et al. is necessary. The method essentially features the method of Kacian et al., but with an additional primer provided to significantly and unexpectedly enhance target amplification at the expense of non-target amplification.

By "oligonucleotide" is meant to include a nucleic acid molecule with at least two nucleoside residues joined through a phosphodiester linkage, or an analog of a phosphodiester linkage known in the art. The nucleotide base moiety of the oligonucleotide may be adenine, guanine, cytosine, thymine, uracil, or other naturally-occurring or synthetic base derivatives, especially those which can complex with a complementary base in another nucleic acid sequence to participate in a double-stranded nucleic acid structure. The sugar moiety may be ribose, deoxyribose, or other derivatives or modified forms of these structures. Many derivatives of the phosphodiester moiety are known in the art and can be used in the invention. An oligonucleotide may also contain domains or residues which are not nucleosides and which might be used, e.g., as a linker to a label or solid support, or to provide other functionality. Oligonucleotides can be synthesized chemically or by use of nucleic acid polymerases, or processed from naturally occurring nucleic acids, by many methods which are well known in the art.

By "primer" is meant a molecule which can be used by a nucleic acid polymerase as a receptor for covalent addition of a suitable nucleoside-5'-phosphoryl (or equivalent) residue. It is convenient to use an oligonucleotide with an extensible 3' end as a primer since it is straightforward to control the sequence of the primer and thus influence the polymerase to copy desired target sequences which are adjacent to sequences complementary to the primer; however, other molecules with priming activity, such as some proteins, are known.

By "promoter-primer" is meant a primer which also has sequence or structural properties which can interact with an RNA polymerase to cause the RNA polymerase to transcribe a desirable template. The promoter-primers used in the examples herein are oligonucleotides which consist of sequences known to be part of an effective promoter for T7 RNA polymerase linked to sequences which are complementary to desired targets in, e.g., the HIV genome. Other promoter sequences are known and can be used including promoters for T3 RNA polymerase and SP6 RNA polymerase. Other strategies can also be employed to promote relatively specific transcription and are intended to be covered by this definition of promoter-primer. For example, an RNA oligonucleotide which is hybridized to a DNA template, especially in a heterotriplex structure (sometimes called an R-Loop) resembling a nascent RNA transcript, can be extended by an RNA polymerase to yield an RNA complement of a desired target template.

By "target region" or "amplification target" is intended to mean a sequence of consecutive nucleotide residues which one desires to amplify by duplication of this sequence or its complement by successive rounds of nucleic acid polymerization. It is not necessary to know the nucleotide sequence of the entire target region but it is helpful to know enough sequence to design at least one complementary primer and a sequence which can be used for specific detection of amplification products, such as by hybridization with a labeled complementary probe.

The phrase "non-target nucleic acid" includes all sequences which are not contained within such a desired target region. These might include, for example, other sequences present on the same genome as the target region, nucleic acids from other genomes or their gene products present in the reaction, such as from a host cell or from environmental contaminants, and nucleic acids deliberately added to the reaction, such as the primers.

In preferred embodiments, the nucleic acid strand is a single-stranded DNA strand or converted to single-strands by denaturing double-stranded DNA; the nucleic acid strand and primers are first contacted at 60° C. or above with an enzyme having DNA polymerase activity active at 60° C. or above; the second contacting step is at 42° C. or above in the presence of a reverse transcriptase and an RNA polymerase; four primers are used in the first contacting step; at least one primer is provided at a concentration different from one other primer; all enzyme activities are provided by a reverse transcriptase and an RNA polymerase; but its enzyme activities may be supplemented by an RNAse H having no DNA polymerase activity; the DNA polymerase lacks 5'-3' exonuclease activity, and is derived from the DNA polymerase I of a *Bacillus* species; e.g.: of the species *Bacillus stearothermophilus* or *Bacillus caldotenax*; the two outside primers hybridize to said nucleic acid strand or its complement at most 2000, 500, or 350 bases apart; and one primer is provided at a concentration between 1 and 10 μM and another said primer is provided at a concentration between 10 and 50 μM.

In other preferred embodiments, two primers are plus-sense primers and the inside plus-sense primer is a promoter-primer; or two primers are minus-sense primers and the outside minus-sense primer is a promoter-primer. References to position and polarity are intended to have the meanings described below in reference to the structures in FIG. 1 and do not depend on polarity designations which might be conventional for the genetic system in which a target region is found. Thus, T74116 and 4195 in FIG. 1 are considered herein to be inside primers; T74312 and/or 4009 are considered to be outside primers. Of the possible amplicons which can result from this array of primers, it is expected that the sequence within the target region delimited by the inside primers will amplify to the greatest extent because amplification products which are delimited by one or both outside primers are targets for annealing by the complementary inside primer but the converse is not necessarily true. Therefore, the target region delimited by the inside primers in FIG. 1 is considered to be the principal target region, and T74116 is an example of the principal promoter-primer.

The sense of the endogenous target region which is complementary to the principal promoter-primer is defined as negative or minus sense, as are other nucleic acids present which have the same sequence sense as the minus target strand. Thus, the principal promoter-primer is defined as positive or plus sense, as are other nucleic acids present that are complementary to the minus sense nucleic acids. It will be apparent to those skilled in the art that these assignments are valid even if the native form of the endogenous template containing the target region is a single-stranded nucleic acid molecule (e.g., RNA) since this strand comprises sufficient information to uniquely specify a complementary strand, and such a complement can be synthesized by the reaction components.

Other features and advantages of the invention will be apparent from the following description of the preferred embodiments thereof and from the claims.

DESCRIPTION OF THE PREFERRED EMBODIMENTS

The drawings will first briefly be described. DRAWINGS

EXAMPLES

The following are non-limiting examples of the present invention. Those in the art will recognize that variations to these examples are within the scope of the appended claims. In particular the specific amounts of reagents and their proportions, and the specific enzymes and nucleic acids used, can be varied to allow amplification of any chosen target. In these examples, certain terms are used as follows.

"Initiation" refers to the process by which an endogenous template sequence is copied or converted into a form which can be transcribed efficiently to yield RNA copies of the target region or its complement (whether this is a desirable target region or not). In the amplification method of Kacian et al., initiation at a particular target is complete when such an RNA product is capable of participating as a template in a cycle of reaction steps, which can lead to de novo formation of a template that can be transcribed to yield an essentially similar RNA molecule. (This RNA molecule may not be identical in sequence to its precursors but retains at least enough sequence similarity to be amplified further).

"Amplicon" refers to a nucleic acid that is a product of one of the reactions in the amplification cycle and which retains the ability to serve as a template for further amplification.

"Pre-initiated template" is used to designate a nucleic acid that possesses the properties of an amplicon, i.e., it can serve as a template for one of the reactions in the amplification cycle without first participating in one of the initiation reactions. A pre-initiated template may indeed be an amplicon product of a prior amplification reaction, or might be constructed synthetically as an experimental model of amplicon activity by methods such as PCR, chemical synthesis or cloning.

As suggested above, the amplification reaction can be perceived as having two phases, one phase including those reaction steps causing the endogenous template to be copied or converted into a functional amplicon, and the second phase including those steps that are part of the inherently cyclical amplification process. The intermediates and products of the amplification steps are essentially similar regardless of the original endogenous template, but the initiation steps used depend on the properties of the endogenous template. Various initiation strategies for the target amplification method of Kacian et al., supra, have been described previously; some of them are described briefly here for convenience and shown diagrammatically in FIG. 2.

Figure 2:
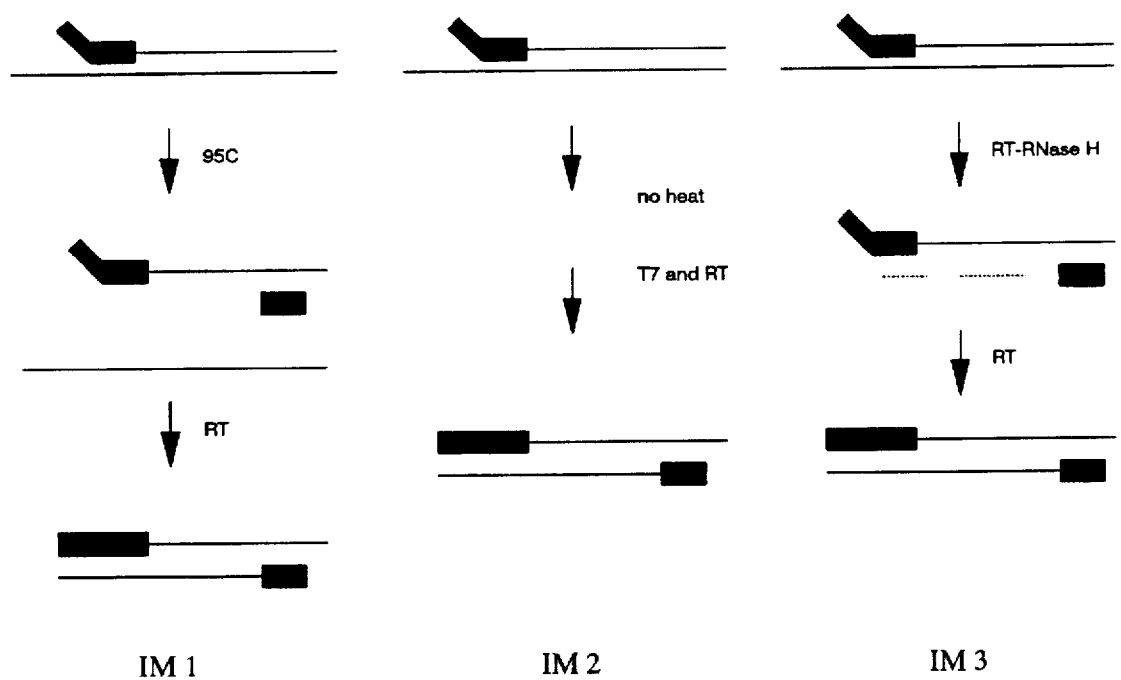
FIG. 2 is a diagrammatic representation of amplification Initiation Methods, IM1, IM2 and IM3 protocols.

Referring to FIG. 2, Initiation Method 1 (IM1) refers to an initiation method in which the endogenous template is DNA. Under conditions allowing a promoterprimer to anneal to a complementary target, a DNA polymerase activity is added to synthesize a complement to the target template by extension of the promoter-primer. The reaction is heated (e.g., at 95° C.) to denature the double-stranded DNA product and cooled to a temperature which allows annealing of a second primer to a complementary sequence on the newly synthesized extension product. When suitable enzymes are added (e.g., RNA polymerase, reverse transcriptase and, optionally, RNase H), the second primer can be extended by DNA polymerase activity to produce a double-stranded copy of the target region linked to a promoter, and thus an active template for the RNA polymerase.

Initiation Method 2 (IM2) refers to an initiation method in which the endogenous template is DNA. A single addition of enzymes (including RNA polymerase, reverse transcriptase and, optionally, RNase H) is sufficient to yield effective initiation even if the reaction is not heated to denature the initial primer extension products. Competent amplicons are generated in the reaction via intrinsic processes in the isothermal reaction.

Initiation Method 3 (IM3) refers to an initiation method in which the endogenous template is RNA. The reaction can be assembled and receive a single enzyme addition (including RNA polymerase, reverse transcriptase and, optionally, RNase H). The double-stranded product of the initial extension of the promoter-primer is an RNA/DNA hybrid. The RNA strand is a substrate for the RNase H activity present and can be degraded to yield a single-stranded copy of the promoter linked to the target region, which in turn is a template for extension of the second primer as described above.

The terms "reaction failure" or "amplification failure" as used herein are not meant to imply that amplification failed to occur but simply that copies of the desired target sequence were not detectable among the products. This may indicate the absence of the desired target among the analyte nucleic acids. This might also result from target-specific initiation or amplification which was not sufficiently effective. For example, target-specific initiation might be ineffective even though many specific initiation events occurred if initiation on non-target sequences yielded excessive competitive amplicons. As will be shown in the examples below, the present invention provides sufficient improvement over existing methods to allow detection of as few as 1–5 copies of a target nucleic acid within a sample without requiring additional heating steps to denature reaction intermediates.

GENERAL METHODS

The procedures described in this section, or slight variations thereof, were used in most of the examples described below. Exceptions and modifications are detailed in each example.

The following is an example of an IM2 amplification reaction.

1) A solution containing the following components was prepared and dispensed in a volume of 25 µl:

200 mM Tris·HCl (pH 8.0 at about 20 °–25° C.)
70 mM MgCl$_2$
8 mM spermidine
0.4 mM deferoxamine mesylate
25 mM each GTP & ATP
10 mM each UTP & CTP
0.8 mM each dATP, dGTP, dCTP, dTTP
0.6 µM T74116 promoter-primer
1.2 µM 4195 primer
20% (v/v) glycerol The primers used in the examples are shown diagrammatically in the figures. They have the following sequences: SEQ. ID NO. 1 (4009): 5'-ATTCCCTACAATCCCCAAAGTCAA-3'; SEQ. ID NO. 2 (T74116): 5'-[AATTTAATACGACTCACTATAGGGAGA]CAAATGGCAGTATTCATCCACA-3'; SEQ. ID NO. 3 (4195): 5'-GTTTGTATGTCTGTTGCTATTAT-3'; and SEQ. ID NO. 4 (T74312): 5'-[AATTTAATACGACTCACTATAGGGAGA]CCCTTCACCTTTCCAGAG-3'. (The promoter sequences are shown in brackets, other promoter can be used in this invention.) The HIV sequences of T74116, 4195 and T74312 were disclosed previously (McDonough et al, U.S. patent application Ser. No. 08/040,745 hereby incorporated by reference herein).

2) To this mixture was added 50 µl of a sample containing the nucleic acids to be analyzed. Model reference system samples contained 1 to 10 µg of purified human white blood cell (WBC) DNA in 80 mM potassium acetate. WBC DNA can be prepared by a variety of well-known methods (See, Maniatis et al., *Molecular Cloning*, a laboratory manual, Cold Spring Harbor Press, Cold Spring Harbor, N.Y., 1982). Alternatively, 50 µl of a hydrolyzed WBC lysate, prepared as described in Example 4, was used. Reactions received 5 µl of water if negative controls, or 5 µl containing a known amount of purified, cloned HIV nucleic acid for testing amplification performance.

3) The mixture was heated to 95° C. and maintained at this temperature for 5 min. It was then transferred to 42° C. and allowed to cool to this temperature.

4) Twenty λl of a solution containing 800 U Moloney MuLV reverse transcriptase (RT) and 400 U T7 RNA polymerase was added in a solution comprising 50 mM Tris·HCl (pH 8.0), 10 mM potassium acetate, 100 mM N-acetyl-L-cysteine and 20% (v/v) glycerol.

5) This was mixed briefly and incubated at 42° C. for 2 hr.

6) The formation of amplification product containing the intended target sequence was determined using a specific hybridization procedure. For all experiments described herein the hybridization protection assay (Arnold et al., *Clin. Chem.* 35:1588 (1989)) and PCT/US88/02746) was used.

Unless specified otherwise in the examples below, the pol1 primers were used in the IM2 experiments at the concentrations listed above (i.e., 15 pmol T74116 and 30 pmol 4195 per 100 µl reaction). When gag11 primers were used, T7811 and 872 were added at 30 pmol each per 100 µl reaction.

Strategies for enhanced initiation effectiveness were tested using the following modifications of the basic IM2 procedure:

1a) A mixture of reaction components was prepared as described in Step 1 in the IM2 procedure. Optionally, additional oligonucleotides were added as outside primers, e.g., 3 pmol each per reaction of 4009 and T74312 for pol1 amplification.

2a) This mixture received 50 µl of a sample containing the nucleic acids to be analyzed. Model reference system samples contained 1 to 10 µg of purified human WBC DNA in 80 mM KOAc. Alternatively, 50 µl of a hydrolyzed WBC lysate, prepared as described in Example 4, was used. Reactions received 5 µl of water for negative controls, or 5 µl containing a known amount of purified, cloned HIV nucleic acid.

3a) The mixture was heated to 95° C. and maintained for 5 min. It was then transferred to 60° C. and allowed to cool to this temperature.

4a) Optionally, 10 µl of a solution containing a thermostable DNA polymerase was added in a solution comprising 50 mM Tris.HCl (pH 8.0), 10 mM potassium acetate, 100 mM N-acetyl-L-cysteine and 20% (v/v) glycerol. Enzymes tested and desirable properties thereof are described in the examples below.

5a) The reaction was mixed briefly and incubated at 60° C. for 10 min.

6a) The reaction was transferred to 42° C. and allowed to cool to this temperature.

7a) 10 µgl of a solution containing 800 U Moloney MuLV reverse transcriptase and 400 U T7 RNA polymerase was added in a solution comprising 50 mM Tris.HCl (pH 8.0), 10 mM potassium acetate, 100 mM N-acetyl-L-cyste-ine and 20% (v/v) glycerol.

8a) The reaction was mixed briefly and incubated at 42° C. for 2 hr.

9a) The formation of amplification product containing the intended target sequence was determined using a specific hybridization procedure such as the hybridization protection assay (Arnold et al., supra).

The outside primers used (if any) and their concentrations are described in each of the examples.

We found that the most valuable indicator of initiation effectiveness was the frequency of reaction failures for a particular template level rather than the extent of amplification in individual reactions. Therefore, for each condition tested, experiments were set up with multiple replicate reactions so that improved initiation effectiveness could be identified by a statistically significant decrease in the failure frequency. Furthermore, the geometric means (G.M.) of the signals for the replicate reactions correlated well with initiation effectiveness and are shown for most of the examples.

The HIV templates used in experiments described in the Examples were purified by standard methods from *Escherichia coli* containing plasmid clones of HIV sequences (see for example Maniatis et al., supra). In experiments specifying BH10 DNA, the template was a purified double-stranded linear DNA having essentially the 8932 nucleotide sequence described in Genbank as HIVBH102 (Accession No. M15654) plus the complementary strand. Other experiments used a linearized plasmid DNA (PUCHIV) comprising the gag and pol genes of BH10 in a standard pUC cloning vector. Both templates had virtually identical template activity per molecule in side by side comparisons.

After purification, the concentration of DNA in these preparations was determined by measuring the amount of 260 nm ultra-violet light absorbed by samples of each preparation ($A_{260}$). The nucleotide sequence, and thus the length, of each of these DNA species is known. The molar concentration for such a preparation was determined by applying standard conversion factors: mass concentration of double-stranded DNA=50 µg ml$^{-1}$ $A_{260}$$^{-1}$; molecular weight of double-stranded DNA=length(bp)×650 g mol$^{-1}$ bp$^{-1}$. A stock solution of template DNA at a concentration $\geq 10^8$ templates per 5 µl (33 pM) was divided into separate aliquots and frozen. For each amplification experiment an aliquot of template was thawed and serially diluted to the desired working concentration (e.g., 5 templates per 5 µl) for addition to reactions. The thawed aliquots and dilutions were discarded after each experiment.

EXAMPLE 1: INITIATION EFFECTIVENESS

To assess quantitatively the effect of various reaction parameters on initiation effectiveness, it was desirable to develop methods to discriminate between changes in amplification effectiveness and in initiation effectiveness in response to a given variable. This was necessary because, for example, we found that conditions favoring optimum amplification performance were not necessarily the conditions which yielded optimum initiation effectiveness. One way we accomplished this was to add pre-initiated templates to reactions as an indicator of the intrinsic amplification performance of various reaction compositions or treatment scenarios and to compare these results with the amplification resulting from addition of a native target sequence.

Using this method, it was possible to determine how rapid and extensive the initiation of target-derived amplicons must be to out-compete the amplification of non-target sequences. An amplification time course was performed in which reactions were assembled according to various desired test conditions but without any target template. At various times after the reaction was started by addition of the RT and RNA polymerase enzymes, template was added and the resulting final amplification extents determined as described below:

1) A mixture was prepared containing the following components, and 85 µl of the solution was dispensed into each reaction tube. The concentrations listed refer to the respective concentrations in the completed 100 µl reaction.

50 mM Tris.HCl (pH 8.0 at room temperature)

17.5 mM MgCl$_2$ 5 mM dithiothreitol 2 mM spermidine 6.25 mM each GTP & ATP 2.5 mM each UTP & CTP 0.2 mM each DATP, dGTP, dCTP, dTTP 0.3 µM each T74116 promoter-primer and 4195 primer 3 µg human WBC DNA 2) The reactions were heated to 95° C. for 7 min, transferred to 37° C. and allowed to cool to this temperature for 5 min.

3) Moloney MULV reverse transcriptase (600 U) and T7 RNA polymerase (400 U) were added to each reaction in 10 µl of buffer (10 mM Tris HCl (pH 8.0), 10 mM potassium acetate and 5 mM dithio-threitol).

4) At various times after enzyme addition, either 100 copies of single-stranded BH10 DNA (purified, cloned HIV DNA, previously denatured by boiling) or 10 copies of pre-initiated template were added to respective reactions in a volume of 5 µl. Three replicates of each time point and condition were processed.

5) After 2 hours the yield of target-specific amplification product determined by the hybridization protection assay (Arnold et al., supra).

Analysis of the geometric mean of the signals of three replicates for each condition shows that even ten (10) pre-initiated amplicons could not be amplified to detectable levels if the amplification biochemistry is allowed to proceed for as few as 10 minutes in the presence of non-target nucleic acids but the absence of target nucleic acid. Furthermore, about ten (10) times more endogenous template was required to achieve an essentially similar time course of amplification as was observed for the pre-initiated template. The difference is explained by the immediate entrance of pre-initiated template into the amplification cycle whereas the non-target amplicons already present continue to accumulate exponentially during the time required for the native template to be copied via the initiation reactions into an amplification competent form. For each of these conditions, more than 90% of the target-specific amplification potential was lost within 3–5 minutes of adding the reverse transcriptase and RNA polymerase to begin the amplification process. The extreme brevity of this window of opportunity for effective initiation was very surprising even though we had expected significant levels of non-target priming and initiation. The trends observed here, as well as in many comparable experiments, suggest that the inhibition was due to excessive depletion of essential reaction components by amplification originating from high levels of non-target initiation.

It has been possible to detect moderately low target levels in many cases using amplification systems developed by routine optimization of methods disclosed by Kacian et al., supra. For example, using the IM2 method and the poll primer set we were able to detect virtually every test sample which contained ≧50 HIV genomes and about ⅔ of the samples containing 20 HIV genomes. This performance reflects very powerful amplification, which would be more than adequate for most purposes. There are, however, cases in which even greater sensitivity is desired. HIV is one example of a pathogen whose nucleic acids might be present at a very low concentration in infected tissues such as whole blood. Reliable detection of HIV nucleic acids sometimes requires a significant sample size (e.g., WBCs from ≧0.1–1 ml blood or more) to ensure that at least one target sequence is present. The nucleic acid extracted from such a sample might contain a single HIV genome in the presence of >20 µg of non-target DNA. The severely aggressive character of competitive non-target amplification as revealed in Example 1 makes it clear that detecting the target in such a sample was a very challenging goal and could not be expected by routine experimentation.

EXAMPLE 2: THERMOSTABLE DNA POLYMERASE

This example demonstrates that significant increases in sensitivity can be achieved by application of the principles disclosed here. Samples A and B, shown in Table 1 were treated using the standard IM2 method as described under General Methods above, i.e. the samples were cooled from 95° C. directly to 42° C. and the reverse transcriptase/T7 RNA polymerase mixture was added to begin the reaction. Samples (C–F) were cooled from 95° C. to 60° C., as described, received 2 U B. stearothermophilus (Bst) DNA polymerase each, and were allowed to incubate for 10 min. The samples were then allowed to cool to 42° C. before receiving the reverse transcriptase/T7 RNA polymerase mixture. Each reaction received purified cloned HIV DNA (pUCHIV) diluted to an average of 5 templates per reaction.

TABLE 1

| Bst | Outside Primers (3 pmol) | | | |
|---|---|---|---|---|
|  | None | T74312 | 4009 | 4009 + T74312 |
|  | A | | | B |
| None | 2,822 | n.d. | n.d. | 5,575 |
|  | 788,364 | | | 1,080,914 |

TABLE 1-continued

| Bst | Outside Primers (3 pmol) | | | |
|---|---|---|---|---|
|  | None | T74312 | 4009 | 4009 + T74312 |
|  | 5,609 | | | 598,645 |
|  | 550,515 | | | 2,904 |
|  | 54,499 | | | 399,264 |
|  | 2,962 | | | 692,780 |
|  | 884,319 | | | 3,057 |
|  | 2,404 | | | 907,013 |
|  | 5,601 | | | 3,386 |
|  | 301,269 | | | 635,132 |
| G.M.: | 36,305 | | | 83,898 |
|  | C | D | E | F |
| 2 U | 2,684 | 894,475 | 996,174 | 1,053,438 |
|  | 21,699 | 1,007,288 | 573,620 | 925,349 |
|  | 500,660 | 10,027 | 933,090 | 985,495 |
|  | 2,685 | 914,272 | 230,777 | 981,515 |
|  | 222,122 | 897,114 | 982,900 | 953,186 |
|  | 157,526 | 923,988 | 701,584 | 1,000,703 |
|  | 518,992 | 942,281 | 802,113 | 1,011,202 |
|  | 318,567 | 962,413 | 939,987 | 1,013,977 |
|  | 736,861 | 963,703 | 3,605 | 958,185 |
|  | 2,896 | 78,465 | 1,100,968 | 1,040,630 |
| G.M.: | 63,108 | 464,691 | 436,989 | 991,645 |

The amount of target sequence generated is expressed in Tables 1–7 in relative light units (RLUs), a measure of the amount of signal obtained from the chemiluminescent label on the detection probe.

The RLU values for the negative control (no pUCHIV) for each of these reaction conditions (A–F) were: 2591, 3097, 2471, 3569, 3459 and 6030, respectively.

These results show that using either a high temperature initiation step with Bst polymerase (C) or including the outside primers even at 42° C. (B) can each alone enhance initiation effectiveness. The most dramatic enhancements were seen when the 60° C. supplemental initiation step was performed in the presence of either of the outside primers (D, E), and the best condition included both outside primers as well as the 60° C. supplemental initiation using Bst DNA polymerase (F).

EXAMPLE 3: PRIMER TITRATION

This example shows some of the surprising properties of the enhanced initiation systems, which make it clear that these enhancements were not obvious nor predictable from prior art.

The most effective concentration of outside primers was determined by titration. In this example, both the T74312 promoter-primer and the 4009 primer were included at equimolar levels as shown in Table 2. The experiment was also intended to determine if initiation enhancement was due primarily to the primer nesting, to the high temperature step alone, to the high temperature incubation in the presence of DNA polymerase, or to some combination of these factors. The reaction condition (A), which had no Bst polymerase and no outside primers, was executed using a standard IM2 initiation as outlined under General Methods above (i.e., no 60° C. step). All the other samples received the 60° C. incubation step whether or not Bst polymerase was included in the reaction.

Each sample shown in the table received an average of 5 molecules of pUCHIV DNA. A negative control was also done for each reaction condition; the RLU values for the negative controls were: 1481, 3073, 1888, 1579, 2150, 1685, and 2038, for A–G, respectively.

TABLE 2

| Bst | Amount of T74312 & 4009 | | | |
|---|---|---|---|---|
| | None | 0.5 pmol each | 1 pmol each | 3 pmol each |
| | A | B | C | D |
| None | 1,539 | 2,613 | 1,839 | 3,196 |
| | 1,817 | 2,798 | 1,968 | 916,062 |
| | 276,389 | 2,618 | 1,859 | 71,336 |
| | 703,977 | 6,461 | 1,735 | 377,802 |
| | 504,437 | 2,499 | 1,827 | 322,609 |
| | 2,190 | 98,767 | 978,524 | 991,897 |
| | 112,011 | 2,563 | 1,767 | 932,431 |
| | 945,321 | 2,362 | 53,199 | 125,527 |
| | 450,767 | 17,165 | 1,713 | 716,442 |
| | 2,021 | 2,234 | 187,509 | 791,526 |
| G.M.: | 47,460 | 4,611 | 7,585 | 264,500 |
| | | E | F | G |
| 2 U | n.d. | 816,921 | 934,499 | 960,554 |
| | | 2,405 | 925,259 | 920,915 |
| | | 990,140 | 992,702 | 952,251 |
| | | 990,692 | 979,840 | 1,012,172 |
| | | 1,008,058 | 966,982 | 954,368 |
| | | 957,396 | 997,355 | 1,011,579 |
| | | 968,449 | 994,863 | 974,269 |
| | | 957,421 | 982,283 | 1,008,390 |
| | | 1,031,290 | 937,674 | 1,017,541 |
| | | 2,055 | 934,387 | 1,023,782 |
| G.M.: | | 285,949 | 946,198 | 982,999 |

As described above, it is possible for the extra primers included in the reaction to inhibit target-specific amplification by promoting additional initiation on non-target sequences. This potential for interference with desired amplification by extra primers in the reaction is observed here, i.e. in the reactions with 0.5 or 1 pmol each outside primer in the absence of the higher temperature pre-initiation step (B, C). In contrast, 3 pmol of each outside primer (D) yielded significantly better initiation effectiveness than the standard IM2 initiation condition (A). The inclusion of the 60° C. primer extension step (E–G) not only broadens the range over which the nested primer strategy is effective, but also, as in the previous example, is synergistic with the best outside primer conditions (G) to yield impressive initiation effectiveness.

EXAMPLE 4: CRUDE LYSATES

This example showed that the initiation enhancements were not only functional, but even more valuable, when applied to a crude lysate typical of a patient sample after appropriate processing. Because of the complex and variable chemical composition of such lysates, it is typical for at least some of the amplification processes to proceed less effectively in lysate than in systems with purified components. Therefore, signals are often lower and/or failures more likely than for comparable target levels in a reaction containing purified components such as the model reference system reaction.

1) Whole blood treated with EDTA as an anticoagulant was mixed with an equal volume of a Density Centrifugation Medium (DCM) comprising PERCOLL in 0.25 M sucrose at a density of 1.110 g/ml. The mixture was centrifuged at 1600×g for 20 min.
2) The mononuclear WBCs (MNC) were harvested by pipetting from a band that formed at the meniscus of the equilibrated mixture. The DCM/MNC suspension was mixed with an equal volume of 0.14 M KOH, mixed well and heated at 95° C. for 30 min.
3) After cooling to room temperature, the resulting hydrolysate was adjusted to pH 8.0±0.5 by adding one-tenth volume of a solution comprising:

0.65 N acetic acid 0.066 M Tris (hydroxymethyl) aminomethane [Tris base]

0.084 M Tris.HCl

4) Amplification reactions received either 50 μl of this lysate or 50 μl of 1 μg of purified human WBC DNA in 80 mM potassium acetate (Reference System).

Test reactions received the number of pUCHIV templates indicated in Table 3. One negative control reaction was done for each condition (A–D) and these values were: 2988, 2179, 5740, and 5602 RLU, respectively.

TABLE 3

| | Standard | Enhanced |
|---|---|---|
| | A | B |
| Reference System | 12,849 | 992,207 |
| 5 pUCHIV | 816,241 | 1,013,207 |
| | 10,397 | 987,214 |
| | 722,462 | 916,050 |
| | 478,359 | 1,004,124 |
| | 890,801 | 980,016 |
| | 615,661 | 951,094 |
| | 2,608 | 1,009,547 |
| | 605,710 | 988,996 |
| | 89,926 | 973,544 |
| | C | D |
| Lysate | 5,381 | 844,281 |
| 10 pUCHIV | 5,604 | 779,576 |
| | 5,568 | 888,957 |
| | 40,029 | 850,735 |
| | 4,980 | 905,316 |
| | 5,245 | 889,550 |
| | 5,385 | 611,966 |
| | 4,826 | 645,488 |
| | 4,937 | 849,922 |
| | 5,067 | 797,581 |

Although the reference system, standard IM2 results (A) showed good initiation effectiveness, it is evident that the enhanced system (B) is significantly better; all 10 signals are essentially saturated under these conditions. Furthermore, the lysate sample results (C, D) make it extremely clear how much benefit can be achieved from using the initiation enhancements.

EXAMPLE 5: OUTSIDE PRIMERS

This experiment re-examined the enhancement obtained with each of the outside primers under the challenging conditions of a low target level (3 pUCHIV) in the presence of lysate. All reactions received 1 U Bst DNA polymerase and were subjected to the 10 minute incubation at 60° C. The outside primers used (at 3 pmol each per reaction) and the combinations tested are shown in the top row of Table 4. The primer 4312b has the identical sequence complementary to HIV as does T74312 but does not have the promoter sequence.

The RLU values obtained from ten (10) replicate reactions for each condition are shown in Table 4. The bottom row of Table 4 shows the geometric mean of the individual replicate results for that condition. The negative control results for each condition (A–E) were 776, 2850, 4053, 3875, and 4126 RLU, respectively.

TABLE 4

| | | Outside Primers | | |
|---|---|---|---|---|
| None | T74312 | 4312b | 4312b & 4009 | T74312 & 4009 |
| 849,178 | 866,790 | 929,644 | 824,030 | 716,145 |
| 3,867 | 804,203 | 3,506 | 4,451 | 910,595 |
| 382,761 | 4,064 | 959,438 | 829,668 | 880,340 |
| 374,433 | 901,779 | 895,765 | 861,299 | 726,859 |
| 284,409 | 896,920 | 3,950 | 240,405 | 922,937 |
| 43,293 | 850,814 | 3,892 | 960,310 | 866,289 |
| 3,893 | 883,606 | 3,637 | 944,199 | 992,987 |
| 3,722 | 1,083,540 | 867,171 | 941,293 | 925,316 |
| 27,165 | 998,443 | 858,293 | 895,293 | 875,782 |
| 893,489 | 920,823 | 930,880 | 909,846 | 958,355 |
| 67,752 | 528,996 | 100,820 | 461,481 | 873,055 |

Figure 3:
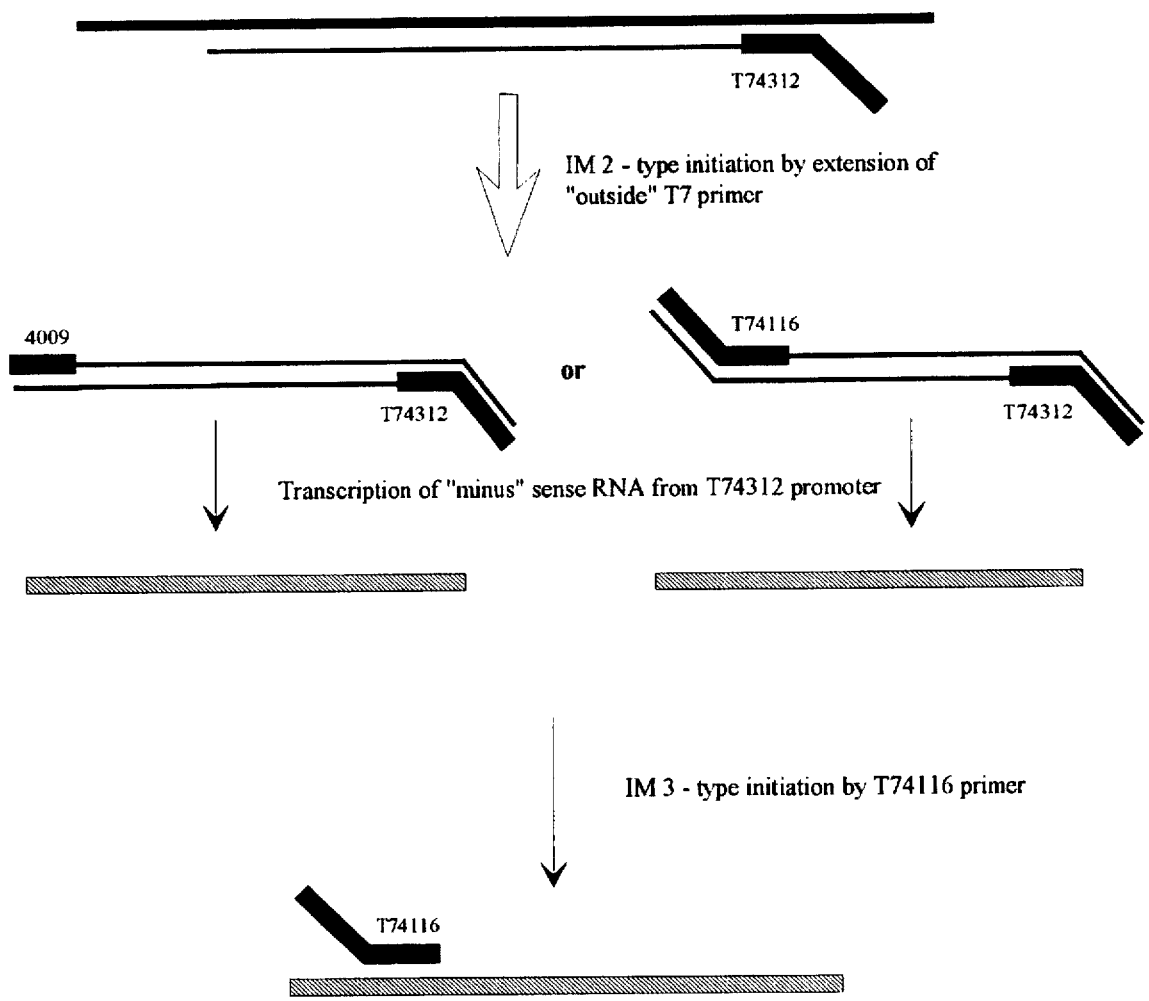
FIG. 3 is a diagrammatic representation showing a possible scheme for initiation by extension of outside T7 primer.

As seen previously in Example 2, these results show that the outside promoter-primer T74312 can promote enhanced initiation even in the absence of 4009. Furthermore, these results strongly suggest that the enhancement potential of T74312 benefits from the promoter moiety since the homologous non-promoter-primer, 4312b, did not stimulate initiation significantly over the control condition with no outside primers. One possible mechanism that could account for these results is shown in FIG. 3. It is likely that T74312 can initiate a IM2 process by being extended on its complement in the usual way. Note that this step should not interfere with the normal initiation steps primed by the principal promoter-primer, T74116, since they occur on different strands.

Initiation by T74312 in this reaction might be expected to be less efficient than by T74116 since T74312 is present at a lower concentration; however, any T74312 initiations that are successfully completed will result in multiple single-stranded RNAs, which are templates for highly efficient IM3-type initiation by T74116, and which can significantly and preferentially accelerate the accumulation of competent poll amplicons during the early stage of the reaction. It probably is desirable for the outside promoter-primer (e.g., T74312) to have lower activity in the reaction than the inside promoter-primer (e.g., T74116) since we have found that highly efficient transcription on both strands can inhibit effective amplification.

Note that different sequences can have different rates of hybridization to their respective complements even at identical concentrations. Therefore the ratio of priming activities for two different oligonucleotide sequences may not be the same as the ratio of their concentrations. However, the molar concentrations are a useful first approximation of the relative activities of two different promoter-primers, and the optimum ratio can be determined by routine experimentation. Furthermore, methods for quantifying hybridization rates are well known in the art and can be used to resolve apparent anomalies in effective concentrations.

It is evident that 4009 improves initiation effectiveness in addition to any role it may serve in completing the formation of transcriptionally-active species initiated by extension of T74312 (diagrammed in FIG. 3). Not only did the presence of 4009 produce a clear enhancement in this experiment even when paired with the non-promoter-primer, 4312b, but it also promoted enhanced initiation in Example 2 in the absence of either 4312 species.

Figure 4:
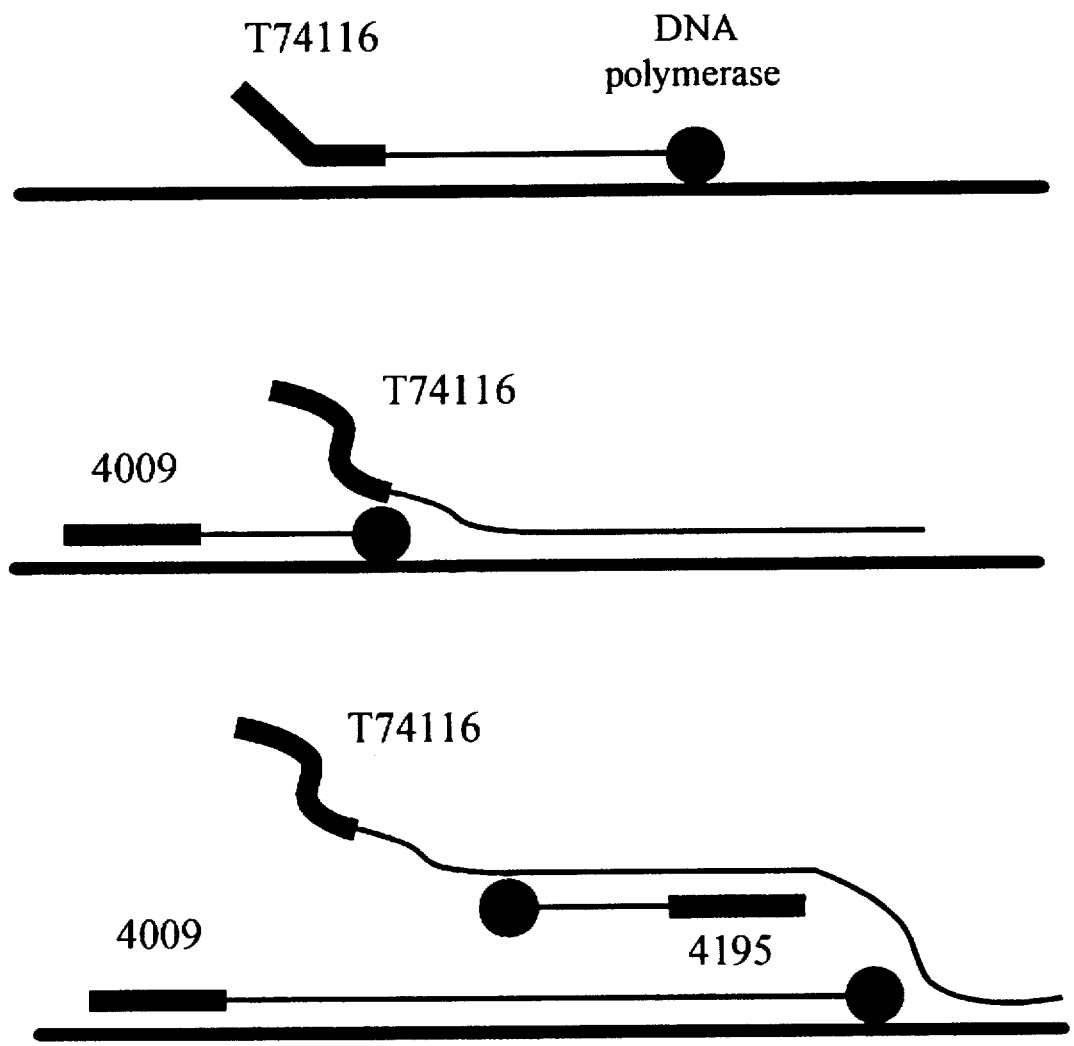
FIG. 4 is a diagrammatic representation showing potential strand displacement activity of T74116 primer extension product by subsequent extension of 4009 primer which may help make target-specific initiation more efficient.

A possible enhancement mechanism consistent with these observations is shown in FIG. 4. Here, primer 4009 is capable of priming DNA synthesis, which can displace previously synthesized DNA extended from the inside promoter primer, T74116. It is desirable that this outside primer have lower activity than the inside promoter-primer to make it less likely that the outside primer will be extended first, rendering the primary target region double stranded and thus inaccessible to initiation by the inside promoter-primer (e.g., T74116).

EXAMPLE 6: DNA POLYMERASE PROPERTIES

The experiments shown in this example were done to determine if properties other than thermostability of the supplemental DNA polymerase were important to the initiation enhancement mechanisms. The results shown in Table 5 were from three different experiments, each with its own goals, but each contained similar controls which can be compared as references to judge the relative merit of each enzyme. The RLU values in the bottom group, labeled "None", were from standard IM2 reactions, incubated with no outside primers and no thermostable DNA polymerase. The middle group, labeled "Bst-1", was treated using the enhanced initiation procedure as described under General Methods and employed Bst DNA polymerase from Bio-Rad. The top group shows the results of the same enhanced initiation procedure substituting one of the alternative thermostable DNA polymerases indicated in the column headings. "Bst-2" denotes a sample of Bst polymerase from a second vendor, Molecular Biology Resources; "Bca" corresponds to DNA polymerase from Bacillus caldotenax (TaKaRa); "REPLITHERM™" is a DNA polymerase available from Epicentre. "KLENTAQ™" DNA polymerase (Ab Peptides) is a derivative of Thermusaquaticus DNA polymerase as described below. The samples were all handled using the enhanced initiation methods described under General Methods. The respective DNA polymerases indicated were used for the 10 minute, 60° C. incubation step. The reactions contained WBC lysates, or were the model reference system and received the average template inoculum shown in Table 5.

TABLE 5

| Reaction: pUCHIV: | Bst-2 Lysate 5 | Bca Model Sys 4 | Replitherm Model Sys 4 | KlenTaq Lysate 5 |
|---|---|---|---|---|
| Test | 1,216,201 | 812,767 | 842,161 | 11,564 |
| Enzyme | 1,041,976 | 801,084 | 818,499 | 811,042 |
| | 952,373 | 851,248 | 1,238 | 153,291 |
| | 1,039,396 | 855,734 | 866,246 | 566,063 |
| | 905,270 | 811,228 | 1,262 | 625,274 |
| | | 846,270 | 865,195 | 427,127 |
| | | 866,044 | 1,455 | |
| G.M.: | 1,025,760 | 834,568 | 52,998 | 245,204 |
| Bst-1 | 547,626 | 944,662 | 944,662 | 906,711 |
| | 276,219 | 913,013 | 913,013 | 891,475 |
| | 710,203 | 906,523 | 906,523 | 654,163 |
| | 19,428 | 921,547 | 921,547 | 33,052 |
| | 728,553 | 954,490 | 954,490 | 813,337 |
| | | 862,586 | 862,586 | 899,851 |
| | | 891,032 | 891,032 | |
| G.M.: | 273,150 | 912,946 | 912,946 | 483,597 |
| None | 3,546 | 855,208 | 855,208 | 5,191 |
| | 3,207 | 1,259 | 1,259 | 5,029 |
| | 3,191 | 849,200 | 849,200 | 5,337 |
| | | 1,334 | 1,334 | 5,417 |
| | | 1,342 | 1,342 | 5,648 |
| | | 1,277 | 1,277 | 5,579 |
| | | 1,461 | 1,461 | |
| G.M.: | 3,311 | 8,441 | 8,441 | 5,363 |

Table 5 shows that several thermostable DNA polymerases other than Bst were also capable of supporting enhanced initiation effectiveness in concert with outside primers. In separate experiments, we found that some other thermostable DNA polymerases did not seem to act synergistically with the nested primers to yield enhanced initiation. These included native DNA polymerases from *Thermus aquaticus* (Taq), *Thermus flavus* (Tfl), *Thermus thermophilus* (Tth), *Thermococcus litoralis* (Vent™, New England Biolabs), or Retrotherm™ (Epicentre). Some of these did confer improved initiation effectiveness compared to standard IM2 if used in an initial 10 minute, 60° C. primer extension step in a reaction without outside primers; however, this improvement was never as extensive as the fully enhanced system described above.

The four polymerase enzymes that did support fully enhanced initiation have at least one property in common, lack of a 5'→3' exonuclease activity which may contribute to their effectiveness. Bst, Bca and KLENTAQ are each homologs of *E. coli* DNA polymerase I. The 5'→3' exonuclease that is usually found in this class of enzyme is removed by proteolysis during purification of Bst by both vendors. Bca and KlenTaq are both manufactured by expression from respective clones of mutant genes defective in this activity. REPLITHERM is reported by its manufacturer to lack any exonuclease activity. That the enhancement mechanism benefits from 5'→3' exonuclease deficiency is suggested here because of this correlation and further corroborated by the superior efficacy of KLENTAQ compared to the native parent form of Taq polymerase.

In these and other experiments, the three polymerases from Bacillus species seemed to support more consistent, stable enhancement than either REPLITHERM or KLENTAQ; therefore, these three related enzymes may share a property that distinguishes them from the other two. One possibility is that efficient strand displacement activity, which is known to differ among DNA polymerases, could contribute to mechanisms such as shown in FIG. 4, but other possibilities are not excluded.

These insights showed that the benefits conferred by the fully-enhanced system were not simply dependent on a brief window of elevated primer annealing stringency enabled by the thermostable DNA polymerase, but that the system as configured here has mechanistic advantages, which were not obvious, nor predictable, from prior art.

EXAMPLE 7: OTHER TARGET REGIONS

Figure 1:
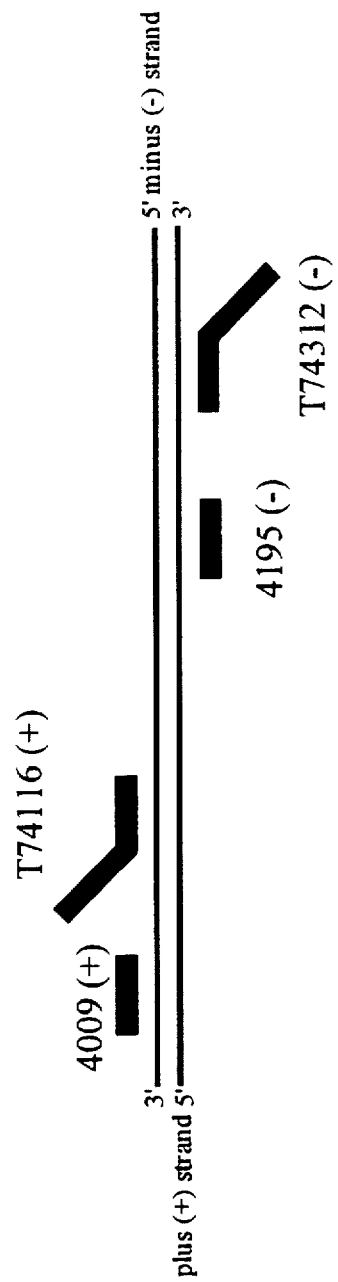
FIG. 1 is a diagrammatic representation of the position of primers relative to the structure of the pol1 target region.

The initiation enhancements were also tested and shown to work for target regions other than pol1. The inside target region shown here is called gag11 and uses the promoter-primer T7811 and the non-promoter primer 872. Primer placement for the nested gag11 target region corresponds to FIG. 1 with 780, T7811, 872, and T71062 substituted for 4009, T74116, 4195, and T74312, respectively. The sequences of these primers are:

SEQ. ID NO. 5 (780): 5'-TGCACCAGGCCAGATGAGAGAACCA-3'

SEQ. ID NO. 6 (T7811): 5'-[AATTTAATACGACTCACTATAGGGAGA]AGTGACATAGCAGGAACTA-3'

SEQ. ID NO. 7 (872): 5'-AGATTTCTCCTACTGGGATAGGT-3'

SEQ. ID NO. 8 (T71062): 5'-[AATTTAATACGACTCACTATAGGGAGA]TTGGACCAGCAAGGTTTCTGTC-3' where the bracketed sequence corresponds to the T7 promoter sequence as described previously (Kacian et al., supra). The promoter portion can be replaced with other functional promoter sequences as described above. The HIV sequences of T7811 and 872 are disclosed in McDonough et al., supra.

In this example, 872 was used at 30 pmol/reaction. The principal promoter-primer, T7811, and the outside primers, T71062 and 780, were present at the indicated concentrations. Otherwise, the reactions were handled as described under General Methods using 1 U of Bst DNA polymerase per reaction.

All reactions contained 50 μl KOH-hydrolyzed lysate as described in Example 4, and positive reactions received an average of 5 pUCHIV templates. Negative control results for each of these conditions (A–H) were 5682, 6501, 5775, 4954, 5689, 5140, 5079, and 4805 RLU, respectively.

TABLE 6

| Principal Promoter | Outside Primers (pmol/100 μl) | | | |
|---|---|---|---|---|
| Primer T7811 | 780: 0<br>T71062: 0 | 5<br>0 | 5<br>5 | 5<br>10 |
| | A | B | C | D |
| 15 | 8,456 | 6,828 | 86,674 | 96,750 |
| | 14,254 | 5,873 | 197,119 | 51,773 |
| | 5,990 | 5,336 | 8885 | 61,521 |
| | 31,141 | 35,033 | 77,964 | 59,049 |
| | 18,771 | 14,259 | 76,564 | 41,677 |
| | 18,517 | 10,092 | 16,734 | 39,743 |
| G.M.: | 14,087 | 10,103 | 49,749 | 55,786 |
| | E | F | G | H |
| 30 | 20,083 | 20,020 | 91,414 | 119,865 |
| | 24,839 | 8,711 | 24,645 | 143,728 |
| | 6,795 | 15,840 | 36,989 | 75,950 |
| | 9,958 | 74,433 | 109,757 | 36,031 |
| | 5,980 | 19,589 | 39,540 | 77,141 |
| | 10,243 | 19,289 | 47,766 | 15,626 |
| G.M.: | 11,287 | 20,657 | 50,843 | 62,005 |

This example shows the benefits of titrating each primer independently. The results of this and other similar experiments are consistent with the expectation, as discussed above, that the optimum concentration of the outside primers should be lower than that of the inside primers. Further optimization improved the gag11 initiation enhancement even more as shown in the data in the next example.

EXAMPLE 8: MULTIPLEX AMPLIFICATION

In some cases it is desirable to amplify two or more distinct target regions in the same reaction. Such "multiplex" amplification reactions, containing 2 or more pairs of primer sets, each delimiting a separate target region, are known in the art. It is most common in such reactions for each target region to amplify less well than if each target region were amplified in separate reactions. Not only do both (or all) true-target amplicons compete with each other for amplification reaction components, but the potential for non-target initiation and competitive amplification should increase as (about) $p_p \times p_t$, where $p_p$ is the total concentration of all promoter-primers in the reaction and $p_t$ is the total concentration of all primers present (or $\sim p_t^2$ in a case such as routine PCR wherein all the primers are functionally equivalent for initiation).

These complications are a significant impediment to routine development of multiplex amplification systems with reliable detection sensitivity for very low template levels. Nevertheless, using the target-specific initiation enhancements described herein, we have been successful in identifying a multiplex reaction composition with high sensitivity for both pol1 and gag11 targets.

Table 7 summarizes the results of one such experiment. Condition A was a standard IM2 procedure in which each of the ten (10) replicate reactions received the pol1 inside primers (T74116 and 4195) and the gag11 primers (T7811 and 872) but no outside primers. After amplification, 50 µl of each reaction was removed and analyzed by hybridization using the pol1 probe. The remaining 50 µl of each reaction was analyzed using the gag11 probe. The results in the pol1 section of column A are arrayed in the same sample order as the gag11 results. (i.e., 50 µl of sample #1 yielded 7,448 RLU when analyzed with the pol1 probe; the remaining 50 µl gave 19,596 RLU when analyzed with the gag11 probe.)

Likewise, the RLU values in column C reflect analysis of half of each respective reaction using the pol1 or gag11 probes as shown. Condition C was the enhanced initiation procedure described under General Methods above except that eight oligonucleotide primers were present (780, T7811, 872, T71062, 4009, T74116, 4195 and T74312, at 5, 30, 30, 10, 3, 15, 30 and 3 pmol/reaction, respectively).

Condition B was the enhanced initiation procedure using only the four pol1 primers, and condition D samples received only the four gag11 primers. Each of the replicate reactions in B and D was analyzed by hybridization using the full reaction volume.

The reactions shown in Table 7 each received an average of 5 pUCHIV templates and 50 µl of lysate prepared as described in Example 4. The corresponding negative controls for these conditions (A, B, C, A', D, and C') were 2094, 2907, 2925, 1799, 2014 and 2315, respectively.

TABLE 7

|       | Multiplex IM2 | Separate Enhanced | Multiplex Enhanced |
|-------|---------------|-------------------|--------------------|
|       | A             | B                 | C                  |
| pol1  | 7,448         | 1,150,134         | 1,078,254          |
|       | 3,397         | 1,201,876         | 1,143,278          |
|       | 3,314         | 1,170,546         | 1,106,627          |
|       | 3,469         | 1,160,177         | 1,112,210          |
|       | 3,314         | 1,143,588         | 1,111,058          |

TABLE 7-continued

|       | Multiplex IM2 | Separate Enhanced | Multiplex Enhanced |
|-------|---------------|-------------------|--------------------|
|       | 3,226         | 1,154,678         | 1,140,999          |
|       | 3,136         | 1,153,301         | 1,118,935          |
|       | 3,192         | 1,195,168         | 3,120              |
|       | 3,185         | 1,178,318         | 1,136,254          |
|       | 151,392       | 1,204,093         | 1,122,474          |
| G.M.: | 5,220         | 1,170,994         | 621,254            |

|       | A'      | D       | C'      |
|-------|---------|---------|---------|
| gag11 | 19,596  | 389,763 | 81,091  |
|       | 2,009   | 327,397 | 92,182  |
|       | 17,717  | 212,354 | 110,175 |
|       | 2,386   | 318,371 | 107,628 |
|       | 2,065   | 345,542 | 74,106  |
|       | 211,008 | 280,156 | 78,950  |
|       | 26,975  | 120,927 | 173,221 |
|       | 84,759  | 323,234 | 2,129   |
|       | 69,965  | 167,985 | 76,044  |
|       | 145,029 | 162,030 | 68,690  |
| G.M.: | 21,018  | 248,238 | 63,089  |

It was apparent from the gag11 results with the enhanced system that this target region amplified to a greater extent in a reaction comprising only gag11 primers (D) than in a reaction comprising pol1 and gag11 primers (C'). Furthermore, it was apparent for both target regions, especially pol1, that detection effectiveness was significantly greater in the enhanced multiplex system (C) than for the multiplex IM2 system (A). Note that the superior initiation effectiveness of gag11 (A') compared to pol1 (A) in standard IM2 is consistent with many previous results.

Baseline signal levels (pol1 RLU=3120, gag11 RLU= 2129) were observed in the same enhanced multiplex samples (C,C') when analyzed by hybridization with each probe, indicating that there was no HIV DNA in these samples to be amplified. A single failure in 10 replicates is not unexpected at the 5 template input level based on the Poisson distribution ($p \geq 0.065$). Therefore, these results indicate that this multiplex system is able to detect single copies of two different target regions in the same reaction.

Other embodiments are within the following claims.

We claim:

1. A method for amplifying a target region present in a target nucleic acid strand using a combination of at least three oligonucleotide primers in a single reaction mixture comprising the steps of:
   (a) contacting a sample comprising said target nucleic acid with said combination, said combination comprising:
      a first oligonucleotide primer comprising a primer region able to hybridize to said target nucleic acid in a first region 3' of said target region,
      a second oligonucleotide primer comprising a primer region able to hybridize to said target nucleic acid in second region 3' of said target region, wherein said second region is 5' of said first region, and
      a third oligonucleotide primer comprising a primer region able to hybridize to a nucleic acid complementary to said target nucleic acid in a first complementary region 3' of a complementary target region,
      wherein said first or second oligonucleotide further comprises a promoter region and said target nucleic acid has not undergone amplification in the absence of said oligonucleotide combination prior to said step (a);
   (b) contacting said sample with one or more proteins having the following enzyme activities:
      (i) an RNA-directed DNA polymerase activity or an DNA-directed DNA polymerase activity or both an RNA directed and DNA-directed DNA polymerase activities,
      (ii) an RNA polymerase activity, and
      (iii) an RNAse H activity; and
   (c) amplifying said target region under primerextension conditions, wherein temperature is not cycled to denature double-stranded primer-extension products during said amplifying step.

2. The method of claim 1, wherein said second oligonucleotide comprises a promoter region, said target nucleic acid is DNA, and prior to said step (b) said target nucleic acid and said oligonucleotide primers are contacted at or above 60° C. with an enzyme having DNA polymerase activity active at or above 60° C.

3. The method of claim 2, wherein said DNA polymerase lacks 5'-3' exonuclease activity.

4. The method of claim 3, further comprising the use of a fourth oligonucleotide primer comprising a primer region able to hybridize to said complementary nucleic acid in a second complementary region, wherein said second complementary region is 3' of said complementary target region and 5' of said first complementary region, and a promoter region.

5. The method of claim 4, wherein said first and said fourth oligonucleotide primers are provided at a lower concentration than said second and third oligonucleotide primers.

6. The method of claim 5, wherein at least one of said first and fourth oligonucleotide primers is provided at a concentration between 1 and 10 µM and at least one of said second and third oligonucleotide primers is provided at a concentration between 10 and 50 µM.

7. The method of claim 6, wherein said first and fourth oligonucleotide primers are provided at a concentration between 1 and 10 µM and said second and third oligonucleotide primers are provided at a concentration between 10 and 50 µM.

8. The method of claim 2, wherein said first oligonucleotide primer is provided at a lower concentration than said second oligonucleotide primer.

9. The method of claim 8, wherein said first oligonucleotide primer is provided at a concentration between 1 and 10 µM and said second oligonucleotide primer is provided at a concentration between 10 and 50 µM.

10. The method of claim 3, wherein said first and said third oligonucleotide primers are outside primers which are no more than 2,000 bases apart.

11. The method of claim 10, wherein said outside primers are no more than 500 bases apart.

12. The method of claim 11, wherein said outside primers are no more than 350 bases apart.

13. A method for amplifying a target region present in a target nucleic acid strand using a combination of at least three oligonucleotide primers in a single reaction mixture comprising the steps of:
   (a) contacting a sample comprising said target nucleic acid with said combination, said combination comprising:
      a first oligonucleotide primer comprising a primer region able to hybridize to said target nucleic acid, in a first region 3' of said target region, and a promoter region,
      a second oligonucleotide primer comprising a primer region able to hybridize to a nucleic acid complementary to said target nucleic acid in a first complementary region 3' of a complementary target region,
      a third oligonucleotide primer comprising a primer region, able to hybridize to said complementary nucleic acid in a second region 3' of said complementary target region, wherein said second complementary region is 5' of said first complementary region,
      wherein said second or said third oligonucleotide further comprises a promoter region and said target nucleic acid has not undergone amplification in the absence of said oligonucleotide combination prior to said step (a):
   (b) contacting said sample with one or more proteins having the following enzyme activities:
      (i) RNA-directed DNA polymerase activity or DNA-directed DNA polymerase activity or both RNA directed and DNA-directed DNA polymerase activities,
      (ii) an RNA polymerase activity, and
      (iii) an RNAse H activity; and
   (c) amplifying said target region under primer-extension conditions, wherein temperature is not cycled to denature double-stranded primer-extension products during said amplifying step.

14. The method of claim 13, wherein said target nucleic acid strand is DNA, said third oligonucleotide comprises a promoter region, and prior to said step (b) said nucleic acid strand and said combination is contacted at or above 60° C. with an enzyme having DNA polymerase activity active at about or above 60° C.

15. The method of claim 14, wherein said DNA polymerase lacks 5'-3' exonuclease activity.

16. The method of claim 15, wherein said third oligonucleotide primer is provided at a lower concentration than said second oligonucleotide primer.

17. The method of claim 16, wherein said second oligonucleotide primer is provided at a concentration between 1 and 10 µM and said third oligonucleotide primer is provided at a concentration between 10 and 50 µM.

18. The method of claim 16, wherein said first and said third oligonucleotide primers are outside primers which are no more than 2,000 bases apart.

19. The method of claim 18, wherein said outside primers are no more than 500 bases apart.

20. The method of claim 19, wherein said outside primers are no more than 350 bases apart.

21. A method for amplifying a target region present in a target nucleic acid using an oligonucleotide combination of at least four oligonucleotide primers in a single reaction mixture comprising the steps of:
  (a) contacting a sample comprising said target nucleic acid with said oligonucleotide combination, said combination comprising:
    a first oligonucleotide primer comprising a primer region able to hybridize to said target nucleic acid in a first region 3' of said target region,
    a second oligonucleotide primer comprising a primer region, able to hybridize to said target nucleic acid in second region 3' of said target region, and a promoter region, wherein said second region is 5' of said first region,
    a third oligonucleotide primer comprising a primer region able to hybridize to a nucleic acid complementary to said target nucleic acid in a first complementary region 3' of a complementary target region,
    a fourth oligonucleotide primer comprising a primer region, able to hybridize to said complementary nucleic acid in second region 3' of said complementary target region, and a promoter region, wherein said second complementary region is 5' of said first complementary region,
    wherein said target nucleic acid has not undergone amplification in the absence of said at least four oligonucleotide primers prior to said first contacting step:
  (b) contacting said sample with one or more proteins having the following enzyme activities:
    (i) RNA-directed DNA polymerase activity or DNA-directed DNA polymerase activity or both RNA directed and DNA-directed DNA polymerase activities,
    (ii) an RNA polymerase activity, and
    (iii) an RNAse H activity; and
  (c) amplifying said target region under primer-extension conditions, wherein temperature is not cycled to denature double-stranded primer-extension products during said amplifying step.

22. The method of claim 21, wherein said target nucleic acid is DNA, and prior to said step (b) said target nucleic acid and said oligonucleotide primers are contacted at or above 60° C. with an enzyme having DNA polymerase activity active at or above 60° C.

23. The method of claim 22, wherein said step (b) is carried out at or above 42° C. in the presence of a reverse transcriptase.

24. The method of claim 22, wherein said target nucleic acid and said primers are heated to 95° C. or higher prior to said step (b).

25. The method of claim 22, wherein one of said first, second, third, and fourth oligonucleotide primers is provided at a concentration different from other said oligonucleotide primers.

26. The method of claim 25, wherein two of said first, second, third, and fourth primers are provided at a concentration different from other said primers.

27. The method of claim 21, wherein at least one of said first and fourth oligonucleotide primers is provided at a concentration between 1 and 10 µM and at least one of said second and third oligonucleotide primers is provided at a concentration between 10 and 50 µM.

28. The method of claim 27, wherein said first and fourth oligonucleotide primers are provided at a concentration between 1 and 10 µM and said second and third oligonucleotide primers are provided at a concentration between 10 and 50 µM.

29. The method of claim 21, wherein all said enzyme activities are provided by a reverse transcriptase and an RNA polymerase.

30. The method of claim 22, wherein said DNA polymerase lacks 5'-3' exonuclease activity.

31. The method of claim 30, wherein said DNA polymerase is derived from a DNA polymerase, which in its natural form possesses 5'-3' exonuclease activity.

32. The method of claim 31, wherein said DNA polymerase is the DNA polymerase I of a Bacillus species.

33. The method of claim 32, wherein said species is *Bacillus stearothermophilus* or *Bacillus caldotenax*.

34. The method of claim 33, wherein said first and said fourth oligonucleotide primers are outside primers no more than 2,000 bases apart.

35. The method of claim 34, wherein said outside primers are no more than 500 bases apart.

36. The method of claim 35, wherein said outside primers are no more than 350 bases apart.

37. A method for enhancing the sensitivity of a transcription-mediated amplification in a single reaction mixture comprising:
  a) contacting a sample containing a target nucleic acid with a combination having at least three oligonucleotides, comprising
    i) a first oligonucleotide having a nucleotide sequence able to hybridize to a first region of a target nucleic acid strand located 3' to a target nucleotide sequence contained on said strand,
    ii) a second oligonucleotide having a nucleotide sequence able to hybridize to a first region of a target-complementary nucleic acid strand located 3' to a target nucleotide sequence contained on said target-complementary strand,
    iii) an oligonucleotide selected from the group consisting of:
      a) a third oligonucleotide having a nucleotide sequence able to hybridize to a second region of said target nucleic acid strand located 3' to said target nucleotide sequence contained on the target strand, wherein said second region of said target strand is located 5' to the first region of said target stand, and
      b) a fourth oligonucleotide having a nucleotide sequence able to hybridize to a second region of said target-complementary nucleic acid strand located 3' to said target nucleotide sequence contained on the target-complementary strand, wherein said second region of said target-complementary strand is located 5' to the first region of said target-complementary strand, wherein either said first or said second oligonucleotide has a 5' promoter sequence, provided if said first oligonucleotide has a promoter sequence, then said fourth oligonucleotide, if present, also has a 5' promoter sequence and if said second oligonucleotide has a promoter sequence, then said third oligonucleotide, if present, also has a 5' promoter sequence, and provided further that said target nucleic acid has not undergone amplification in the absence of said combination prior to step a):

b) contacting said sample with one or more proteins having the following enzyme activities:
  i) an RNA-directed DNA polymerase activity, or a DNA-directed DNA polymerase activity, or both RNA-directed DNA polymerase and DNA-directed DNA polymerase activities,
  ii) an RNA polymerase activity
  iii) an RNAse H activity, and c) amplifying said target region without temperature cycling to cause thermal denaturation of double-stranded primer extension products.

38. The method of claim 37 wherein said composition comprises said first, second, third and fourth oligonucleotides.

39. The method of claim 37 further comprising incubating said target nucleic acid and said composition at about 60° C. or above prior to said amplifying step.

40. The method of claim 39 further comprising contacting said target nucleic acid and said composition with a DNA polymerase active at about 60° C. or above.

41. The method of claim 40 wherein said DNA polymerase is selected from either a DNA polymerase derived from DNA polymerase I or a Bacillus species.

42. The method of claim 40 in which the DNA polymerase lacks a 5'-3' exonuclease activity.

43. The method of claim 37 wherein said third or fourth oligonucleotide is provided in a higher concentration then either said first or second oligonucleotide.

44. The method of claim 38 wherein said third and fourth oligonucleotides are each provided in a higher concentration than each of said first or second oligonucleotide.

45. The method of claim 43 wherein said first oligonucleotide has a 5' promoter region and is provided at a lower concentration than said second oligonucleotide.

46. The method of claim 44 wherein said first oligonucleotide has a 5' promoter region and is provided at a lower concentration than said second oligonucleotide.

47. The method of claim 43 wherein said second oligonucleotide has a 5' promoter region and is provided at a lower concentration than said first oligonucleotide.

48. The method of claim 44 wherein said second oligonucleotide ha s a 5' promoter region and is provided at a lower concentration than said first oligonucleotide.

49. The method of claim 45 wherein said third or fourth oligonucleotide is provided at about a ten-fold higher concentration than said first oligonucleotide.

50. The method of claim 46 wherein said third and fourth oligonucleotides are each provided at about a ten-fold higher concentration than said first oligonucleotide.

51. The method of claim 45 wherein said third or fourth oligonucleotide is provided at about a ten-fold higher concentration than said second oligonucleotide.

52. The method of claim 46 wherein said third and fourth oligonucleotides are each provided at about a ten-fold higher concentration than said second oligonucleotide.

53. The method of claim 49 wherein said oligonucleotides are each present in the range of about 30 to about 300 nM.

54. The method of claim 51 wherein said oligonucleotides are each present in the range of about 30 to about 300 nM.

55. The method of claim 37 wherein said sample contains about 5–50 copies of the target nucleotide sequence.

56. The method of claim 55 wherein said sample contains about 5–20 copies of the target nucleotide sequence.

57. The method of claim 56 wherein said sample contains about 5 copies of the target nucleotide sequence.

58. The method of claim 37 further comprising raising the temperature of the sample and combination to denature double-stranded nucleic acids prior to step c.

59. The method of claim 40 further comprising raising the temperature of the sample and combination to denature double-stranded nucleic acids prior to said incubating step.

* * * * *

UNITED STATES PATENT AND TRADEMARK OFFICE
CERTIFICATE OF CORRECTION

PATENT NO. : 5,786,183
DATED : July 28, 1998
INVENTOR(S) : Thomas B. Ryder et al.

It is certified that error appears in the above-identified patent and that said Letters Patent is hereby corrected as shown below:

Column 23, Line 41: delete "primerextension" and insert --primer-extension--

Signed and Sealed this

Thirtieth Day of March, 1999

Attest:

Attesting Officer

Q. TODD DICKINSON

Acting Commissioner of Patents and Trademarks